(12) United States Patent
Argillier et al.

(10) Patent No.: US 10,745,298 B2
(45) Date of Patent: Aug. 18, 2020

(54) METHOD FOR TREATING AN AQUEOUS LIQUID BY MEANS OF A FILTER DETERMINED AS A FUNCTION OF THE INTERFACIAL TENSION OF THE LIQUID

(71) Applicant: IFP Energies nouvelles, Rueil-Malmaison (FR)

(72) Inventors: Jean-Francois Argillier, Rueil-Malmaison (FR); Antoine Benoit, Maule (FR); Isabelle Henaut, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 170 days.

(21) Appl. No.: 15/839,231

(22) Filed: Dec. 12, 2017

(65) Prior Publication Data
US 2018/0162751 A1 Jun. 14, 2018

(30) Foreign Application Priority Data

Dec. 14, 2016 (FR) ..................................... 16 62413

(51) Int. Cl.
| | |
|---|---|
| C02F 1/44 | (2006.01) |
| G01N 11/02 | (2006.01) |
| G01N 33/24 | (2006.01) |
| B01D 69/02 | (2006.01) |
| B01D 71/02 | (2006.01) |
| B01D 71/06 | (2006.01) |
| C09K 8/584 | (2006.01) |
| C10G 49/22 | (2006.01) |
| G01N 13/02 | (2006.01) |
| C10G 33/00 | (2006.01) |
| B01D 17/00 | (2006.01) |
| B01D 17/12 | (2006.01) |
| C02F 103/36 | (2006.01) |
| G01N 11/00 | (2006.01) |
| C02F 101/32 | (2006.01) |
| E21B 43/16 | (2006.01) |

(52) U.S. Cl.
CPC .............. *C02F 1/44* (2013.01); *B01D 17/085* (2013.01); *B01D 17/12* (2013.01); *B01D 69/02* (2013.01); *B01D 71/022* (2013.01); *B01D 71/06* (2013.01); *C09K 8/584* (2013.01); *C10G 33/00* (2013.01); *C10G 49/22* (2013.01); *G01N 11/02* (2013.01); *G01N 13/02* (2013.01); *G01N 33/241* (2013.01); *B01D 2315/08* (2013.01); *B01D 2315/10* (2013.01); *B01D 2325/02* (2013.01); *C02F 2101/32* (2013.01); *C02F 2103/365* (2013.01); *E21B 43/16* (2013.01); *G01N 2011/006* (2013.01); *G01N 2013/0275* (2013.01)

(58) Field of Classification Search
None
See application file for complete search history.

(56) References Cited

U.S. PATENT DOCUMENTS

| | | | |
|---|---|---|---|
| 4,655,927 A | 4/1987 | Ford | |
| 2009/0241496 A1 | 10/2009 | Pintault et al. | |
| 2011/0124941 A1* | 5/2011 | Verdegan | B01D 17/045 585/818 |
| 2013/0149745 A1 | 6/2013 | Cheon et al. | |
| 2014/0332462 A1 | 11/2014 | Solomon et al. | |

OTHER PUBLICATIONS

Aronson, "The Role of Free Surfactant in Destabilizing Oil-in-Water Emulsions," American Chemical Society, 1989.*
Extended European Search Report for 16/62.413 (6 Pgs.).

* cited by examiner

Primary Examiner — Krishnan S Menon
(74) Attorney, Agent, or Firm — Fitch, Even, Tabin & Flannery, LLP

(57) ABSTRACT

The present invention relates to a method for treating an aqueous liquid comprising oil droplets and a surfactant and/or a base. For this method, a pore size threshold of a filter is determined taking into account the interfacial tension between the oil droplets and the water, and a filter is selected whose pore size is less than or equal to this threshold for filtration of the aqueous liquid.

9 Claims, No Drawings

METHOD FOR TREATING AN AQUEOUS LIQUID BY MEANS OF A FILTER DETERMINED AS A FUNCTION OF THE INTERFACIAL TENSION OF THE LIQUID

The present invention relates to the field of water treatment, notably by filtration, in particular in the field of hydrocarbon deposit exploitation.

CROSS-REFERENCE TO RELATED APPLICATIONS

This application claims the benefit of French Patent Application No. 16/62.413 filed Dec. 14, 2016, the contents of which is incorporated herein by reference as if fully rewritten herein.

Until recently, exploitation of a so-called conventional oil field commonly proceeded in two stages: a first stage of primary recovery based purely on the increased pressure present in the reservoir, followed by a second stage generally using waterflooding. This method consists of injecting water into the underground formation in order to compensate the pressure drop in the reservoir, and therefore remobilize the oil in situ. This water, as well as the water that may be present initially in the underground formation, will be present in the petroleum effluents. It is therefore necessary to treat these petroleum effluents so that only the hydrocarbons are recovered. The first step in the treatment of the petroleum effluents generally consists of separating the water and the oil by gravity (for example by a "Free-Water Knock-Out" method). The oil thus recovered is sent to desalination and dehydration operations. Moreover, the water separated from the oil is not completely clean (the gravity separation process is not perfect): notably it contains oil droplets and impurities. To remove these impurities and the oil droplets, the water is sent to water treatment operations, notably deoiling operations. At the end of the water treatment operations, the water quality must be sufficient to meet the legal norms or must be suitable for reinjection into the underground formation.

Currently, petroleum engineers aim to optimize recovery of the hydrocarbons. This can be achieved by decreasing the residual oil saturation obtained at the end of the waterflooding operation, which on average is 65% for the reservoirs that are preferentially wettable with water. To meet this objective, new techniques have been developed, called chemical tertiary recovery (or Chemical Enhanced Oil Recovery, cEOR). These processes are based on the addition of additives to the water injected for waterflooding, such as polymers, surfactants, alkalies or a combination of these additives. Now, after percolation of this solution to the producing well, it has been demonstrated that the properties of the effluent produced at the wellhead are modified by the additives (polymers, surfactants and/or alkalies), making the existing separation processes inefficient.

In particular, for water treatment, the operations of water filtration are usually carried out with filters having pores whose radii are selected to be slightly smaller than the radii of the oil droplets contained in the water, so that these oil droplets are retained. However, this criterion is no longer valid when the water to be purified contains surface-active substances and/or bases resulting from assisted recovery of hydrocarbons. In fact, in this case, it is found that the oil droplets can pass through pores of smaller radius than the diameter of the droplets.

As an example, water containing 200 ppm of droplets of crude (i.e. oil) with a diameter of 15 μm with different concentrations of surface-active agent (also called surfactant) C12Tab, was filtered on a filter with a pore diameter of 5 μm. Dead-end filtration is used (for this example). The results (oil content in the filtrate, i.e. the content of oil in the filtered water) are presented in Table 1, and show that the presence of the surfactant makes filtration ineffective above 200 ppm of surfactant.

TABLE 1

| Filtration on a 5-μm membrane | | | | |
|---|---|---|---|---|
| Concentration of C12TAB (ppm) | 50 | 100 | 200 | 500 |
| Oil content in the filtrate (ppm) | 21 | 25 | 167 | 197 |

To overcome these drawbacks, the present invention relates to a method for treating an aqueous liquid comprising oil droplets and a surfactant and/or a base. For this method, a pore size threshold of a filter is determined, taking into account the interfacial tension between the oil droplets and the water, and a filter is selected for which the pore size is less than or equal to this threshold for filtration of the aqueous liquid. By taking into account the interfacial tension, which is related to the presence of surfactant and/or base, it is possible to take into account the deformation of the droplets, and therefore adapt the pores of the filter to the composition of the aqueous liquid. It is thus possible to maintain effective filtration of the aqueous liquid.

The Method According to the Invention

The invention relates to a method for treating an aqueous liquid, said aqueous liquid comprising oil droplets and at least one surfactant and/or at least one base. For this method, the following steps are carried out:
   a) determining the interfacial tension between said oil droplets and the water in said aqueous liquid, said interfacial tension being dependent upon said surfactant and/or said base;
   b) determining a pore size threshold of a filter for retaining said oil droplets from said aqueous liquid, said pore size threshold being a function of said interfacial tension; and
   c) treating said aqueous liquid by filtration using a filter for which the size of said pores is less than or equal to said pore size threshold.

According to one embodiment of the invention, said pore size threshold of said filter is determined by means of a threshold capillary number.

According to one embodiment of the invention, said threshold of size of said pores $R_{def}$ is determined from a formula of the type $$R_{def} = Ca^* \frac{\Gamma}{\eta \dot{\gamma}},$$

where $\eta$ is the viscosity of said aqueous liquid, $\dot{\gamma}$ is said shear rate applied to an oil droplet, $\Gamma$ is the interfacial tension and $Ca^*$ is said threshold capillary number.

According to an optional embodiment, said threshold capillary number is determined by applying the following steps:
   i) determining the viscosity $\eta$ of said aqueous liquid, the shear rate applied to an oil droplet $\dot{\gamma}$ the droplet radius R and the interfacial tension $\Gamma$ for filtration of said aqueous liquid in a filter whose pores are of a specified size; and ii) calculating said threshold capillary number Ca* using a formula of the type:

$$Ca^* = \frac{\eta \dot{\gamma} R}{\Gamma}.$$

Advantageously, said viscosity of said aqueous liquid is determined by measurement, notably using a rheometer.

Preferably, said interfacial tension is determined by measurement, or as a function of said concentration and of the type of said surfactant and/or of said base.

According to one feature, said shear rate is determined as a function of the flow rate of said aqueous liquid in said filter.

Advantageously, said filtration is dead-end or tangential membrane filtration with flow of said aqueous liquid.

According to one embodiment, said filter is a polymeric, or metallic or ceramic membrane.

Moreover, the invention relates to a method for treating a petroleum effluent. For this method, the following steps are carried out:
  a) separating the phases of said petroleum effluent, to separate at least an aqueous liquid phase, a liquid oil phase and a gas phase; and
  b) treating said aqueous liquid phase by the method for treating an aqueous liquid according to one of the preceding features, said aqueous liquid comprising oil droplets and at least one surfactant and/or base of said injected fluid.

Furthermore, the invention relates to a method of assisted recovery of hydrocarbons from an underground formation. For this method, the following steps are carried out:
  a) injecting a fluid into said underground formation, said injected fluid comprising at least one surfactant and/or base;
  b) recovering a petroleum effluent from said underground formation, said petroleum effluent comprising at least one part of said injected fluid;
  c) separating the phases of said petroleum effluent, to separate at least an aqueous liquid phase, a liquid oil phase and a gas phase; and
  d) treating said aqueous phase by the method for treating an aqueous liquid according to one of the preceding features, said aqueous liquid comprising oil droplets and at least one surfactant and/or base of said injected fluid.

DETAILED DESCRIPTION OF THE INVENTION

The present invention relates to a method for treating an aqueous liquid. The aqueous liquid essentially comprises water, some oil droplets (for example up to 500 ppm), and at least one surfactant and/or at least one base (for example an alkali). The liquid may comprise other elements in small amounts, such as polymers, weighting materials, etc.

The method of treatment according to the invention aims to limit the amount of oil droplets in the water. This limiting of the amount of oil in the water is accomplished by means of a filter, with the liquid circulating in the filter through pores. The pores make it possible to limit the passage of oil droplets mechanically. The aqueous liquid may be a liquid resulting from gravity separation of oil and water of a petroleum effluent. However, the method according to the invention is suitable for any type of aqueous liquid comprising oil droplets and at least one surfactant and/or base.

It will be recalled that a surface-active agent or surfactant is a compound that alters the surface tension between two surfaces. Surface-active compounds are amphiphilic molecules, i.e. they have two parts with different polarity, one lipophilic (which retains oily substances) and nonpolar, the other hydrophilic (water-miscible) and polar. They thus make it possible to stabilize a mixture of two immiscible phases, by interacting with one that is nonpolar (i.e. lipophilic and therefore hydrophobic), by its hydrophobic part; whereas it will interact by its hydrophilic part with the other phase, which is polar. The following surfactants may be mentioned, nonexhaustively: nonyl phenol ethoxylates (Triton X100), sorbitan ester (Tween 20), alkyl betaines (Mackamine C10), sodium dodecylbenzene sulfonate (SDBS).

The base contained in the water may be an alkali. According to a nonlimiting example, the base may be $Na_2CO_3$, NaOH etc.

According to the invention, a threshold size of the pores (also called pore size threshold, or "pore throat") is defined to allow said separation of the oil droplets. The term size defines a dimension of the pore, in particular a radius (or diameter) of the pore. The pore size threshold according to the invention is defined taking into account the interfacial tension between the oil droplets and the water. It will be recalled that the interfacial tension is the ratio of the reversible work supplied for extending a fluid-fluid separation interface (here oil and water) to the corresponding extension of the interface, other things being equal. The interfacial tension depends notably on the type of oil, the type of surfactant, the concentration of the surfactant, the presence or absence of a base, and the concentration of base. By taking into account the surfactant and/or the base, it is possible to take into account the deformability of the oil droplets, said deformability allowing the oil droplets to enter the pores of the filter of smaller diameter (cf. Table 1 in the introduction). Thus, the method according to the invention makes it possible to dimension a filter that is efficient for separating the oil droplets; the pores are dimensioned taking into account the deformability of the droplets.

The method according to the invention comprises the following steps:
  1. Determination of the interfacial tension
  2. Determination of the pore size threshold of the filter
  3. Filtration of the liquid
  1. Determination of the Interfacial Tension The interfacial tension between the oil droplets and the water of the aqueous liquid is determined in this step. This step makes it possible to take into account the surfactant and/or the base present in the aqueous liquid.

According to a first embodiment of the invention, the interfacial tension between the oil droplets and the water can be determined by measuring the interfacial tension, for example by pendant drop or spinning drop methods of measurement, depending on the order of magnitude of the interfacial tensions.

According to a second embodiment of the invention, the interfacial tension can be determined using nomograms or on the basis of data supplied by the manufacturer, taking into account the type of surfactant, and its concentration in the aqueous liquid. Advantageously, determination of the interfacial tension may also take into account the presence of a base in the aqueous liquid. In fact, the presence of a base, for example the presence of $Na_2CO_3$, lowers the interfacial tension depending on the composition of the oil (also called crude), in particular for reactive crudes, i.e. sour, heavy or asphaltene crudes that contain acids that are saponifiable in the presence of a base.

2. Determination of the Pore Size Threshold

In this step, the pore size threshold of a filter that will be able to retain the oil droplets of the aqueous liquid is determined, taking into account the deformability of the droplets, i.e. the interfacial tension.

Conventionally, for the pore size threshold, a pore radius or diameter is determined. This pore size threshold of the filter corresponds to the "deformable radius/diameter" of the oil droplets, in other words the equivalent radius or diameter of an oil droplet subjected to a specified interfacial tension. The pore size threshold is generally between 0.001 and 20 µm.

Advantageously, the pore size threshold of the filter may depend on the flow rate of the aqueous liquid in the filter.

According to one embodiment of the invention, the pore size threshold can be determined by means of a threshold capillary number. Advantageously, the threshold capillary number can be obtained by a filtration test of an aqueous liquid. The filtration test can be carried out using a filter with a known pore diameter, and preferably with an aqueous liquid comprising little or no surfactant and/or base.

Next, the pore size threshold (for example the radius $R_{def}$ or the diameter $D_{def}$) can be determined from the threshold capillary number $Ca^*$ and the interfacial tension $\Gamma$ determined in the preceding step, with a formula of the type:

$$R_{def} = Ca^* \frac{\Gamma}{\eta \dot{\gamma}}$$

or, if applicable, $$D_{def} = 2Ca^* \frac{\Gamma}{\eta \dot{\gamma}},$$

where $\eta$ is the viscosity of the aqueous liquid, $\dot{\gamma}$ is the shear rate applied to an oil droplet (which may depend on the flow rate of the aqueous liquid in the filter), $\Gamma$ is the interfacial tension determined in the preceding step and $Ca^*$ is the threshold capillary number.

According to one embodiment of the invention, the threshold capillary number can be determined by means of a test, using the following steps:

i) for efficient filtration (i.e. for which filtration of the oil droplets is provided by the filter) of the aqueous liquid in a filter with pores of a specified size, the following are determined:
the viscosity $\eta$,
the shear rate applied to an oil droplet $\dot{\gamma}$,
the droplet radius R (or its diameter D if applicable) and the interfacial tension $\Gamma$ determined in the preceding step; and ii) for this test, the threshold capillary number $Ca^*$ is calculated using a formula of the type:

$$Ca^* = \frac{\eta \dot{\gamma} R}{\Gamma}$$

(or if applicable $$Ca^* = \frac{\eta \dot{\gamma} D}{2\Gamma}).$$

The viscosity can be determined by measurement, notably using a rheometer. According to one embodiment of the invention, the viscosity may be considered identical for the test case and for the case to be filtered. In this case, since this parameter appears both in the equation for determining the threshold capillary number and in the equation for the pore size threshold, it is not necessary to know it.

The shear rate depends notably on the volume flow rate of the liquid through the filter. For example, the shear rate can be determined from a formula of the type $$\dot{\gamma} = \beta \frac{4Q}{S\varphi r_h}$$

where Q is the volume flow rate, $\varphi$ is the porosity, S is the filtration cross section, $\beta$ is an experimental calibration parameter and $r_h$ is the hydrodynamic radius of the pores (this formula is notably illustrated in more detail in the document Chauveteau G.: "Rodlike Polymer Solution Flow through Fine Pores: Influence of Pore Size on the Rheological Behavior", J. Rheol., 26, 2, p. 111-142, 1982). According to one embodiment of the invention, the shear rate may be considered identical for the test case and for the case to be filtered (as the flow rate is assumed constant). In this case, since this parameter appears both in the equation for determining the threshold capillary number and in the equation for the pore size threshold, it is not necessary to know it.

The radius of the oil droplets (or their diameter if applicable) can be determined for the example using a granulometer based on light scattering, or any similar means.

3. Filtration of the Aqueous Liquid

In this step, filtration of the aqueous liquid is carried out using a filter whose pore size is less than or equal to (preferably strictly less than) the pore size threshold determined in the preceding step.

To increase filtration efficiency, the pore size of the filter may be less than 0.9 times the pore size threshold determined in the preceding step.

According to one embodiment of the invention, dead-end or tangential membrane filtration is carried out with flow of the aqueous liquid. The filtration membrane may be a polymer membrane, or a metallic membrane, or a ceramic membrane.

Thus, at the end of the filtration step according to the method of the invention, a high proportion of the oil droplets are blocked by the filter, the water recovered is of better quality, and requires little additional treatment to comply with the current environmental standards.

The invention also relates to a method for treating a petroleum effluent. "Petroleum effluent" means a fluid recovered by a producing well in a method for recovery of hydrocarbons from an underground formation. A petroleum effluent generally comprises oil (hydrocarbons in liquid form), gas (hydrocarbons in gaseous form) and water, as well as at least part of a flushing fluid injected into the formation in order to recover the hydrocarbons.

The method for treating a petroleum effluent may comprise at least the following steps:
a) separating the phases of the petroleum effluent, to separate at least one aqueous liquid phase, an oil liquid phase, and a gas phase; this separation may be gravity separation, for example of the "Free-Water Knock-Out" type. At the end of this step, the aqueous liquid essentially comprises water, oil droplets, and at least one surfactant and/or base.

b) treating the aqueous liquid resulting from the separation by a method for treating aqueous liquid according to one of the features described above, taking into account the surfactant and/or the base present in this aqueous liquid. The water quality is thus improved.

The method for treating the petroleum effluent may further comprise a step of treatment of the gas resulting from the separation.

Moreover, the method for treating the petroleum effluent may comprise steps of treatment of the oil resulting from the separation. These steps of treatment of the oil may be steps of dehydration, desalting, etc.

Furthermore, the invention relates to a method of assisted recovery of hydrocarbons from an underground formation. The method of assisted recovery of hydrocarbons comprises at least the following steps:

a) injecting a fluid into the underground formation, via an injection well, the injected fluid comprising at least one surfactant and/or base (for example an alkali); the injected fluid may also comprise polymers;

b) recovering a petroleum effluent from the underground formation, via a producing well, the petroleum effluent comprising at least one part of the injected fluid, i.e. a part of the surfactant, of the polymers and/or of the alkalies;

c) separating the phases of the petroleum effluent, to separate at least an aqueous liquid phase, a liquid oil phase and a gas phase; this separation may be gravity separation, for example of the "Free-Water Knock-Out" type. At the end of this step, the aqueous liquid essentially comprises water, oil droplets, and at least one surfactant and/or base; and d) treating the aqueous phase by the method for treating an aqueous liquid described above, the aqueous liquid comprising at least one surfactant and/or base of the injected fluid. The water quality is thus improved.

The method of assisted recovery of hydrocarbons may further comprise a step of treatment of the gas resulting from the separation.

Moreover, the method of assisted recovery of hydrocarbons may comprise steps of treatment of the oil resulting from the separation. These steps of treatment of the oil may be steps of dehydration, desalting, etc.

EMBODIMENT EXAMPLES

The features and advantages of the method according to the invention will become clearer on reading the embodiment examples given below.

First Example

The first example is based on the example in Table 1 of the introduction, with a concentration of 200 ppm of surfactant C12TAB. It will be recalled that in Table 1, the water contained 200 ppm of droplets of crude (of oil) with a diameter of 15 μm (radius 7.5 μm), the pores of the filter had a diameter of 5 μm (radius 2.5 μm). Moreover, the filter used was efficient with a concentration of surfactant of 50 ppm (first column of Table 1), i.e. with an interfacial tension of 3 mNm. The viscosity of the aqueous liquid is about 1 cP.

The method according to the invention is applied:

1. the interfacial tension of the oil droplets with 200 ppm of surfactant C12TAB is 0.5 mNm.
2. The threshold capillary number is calculated from the first column of Table 1, i.e.:

$$Ca^* = \frac{\eta \dot{\gamma} D}{\Gamma} = \frac{10^{-2} \dot{\gamma} 15 \cdot 10^{-6}}{3 \cdot 10^{-3}} = \dot{\gamma} \cdot 5 \cdot 10^{-5}$$

The pore size threshold (by diameter) for a concentration of surfactant of 200 ppm is then:

$$D_{def} = Ca^* \frac{\Gamma}{\eta \dot{\gamma}} = \dot{\gamma} \cdot 5 \cdot 10^{-5} \frac{0.5^{-3}}{10^{-2} \dot{\gamma}} = 2.5 \cdot 10^{-6}$$

Consequently, the threshold diameter of the pores is 2.5 μm, i.e. a threshold radius of 1.25 μm.

Determination of this new threshold diameter makes it possible to select new membranes with a suitable pore size, i.e. pores with a diameter less than 2.5 μm. Two membranes with pore diameters equal to 1.2 μm and 0.2 μm were then used and gave correct water quality (cf. Table 2), which reflects good filtration efficiency.

TABLE 2

| First example | | | |
|---|---|---|---|
| Diameter of the pores (μm) | 5 | 1.2 | 0.2 |
| Oil content in the filtrate (ppm) | 167 | 30 | 11 |

Second Example

As the second example, water containing 200 ppm of droplets of crude (of oil) with a diameter of 8 μm with 7 g/L of $Na_2CO_3$ was filtered. The results are presented in Table 3 and show that the presence of the base lowers the oil/water interfacial tension and makes filtration inefficient if the pore size is not reduced in view of the deformability conferred on the droplets $D_{def}$ (0.3 μm for the average value) calculated by the method according to the invention on the basis of the threshold capillary number for the case of water without alkali (column on the right of the table). It will be noted that the filter that is efficient in this case is the filter having pores with a diameter of 0.2 μm. This table shows the minimum, average and maximum values of the diameter of deformability of the droplets, to take into account the droplet size distribution representative of the oil droplets present in the aqueous liquid.

TABLE 3

| Second example | | | | |
|---|---|---|---|---|
| $Na_2CO_3$ concentration (g/L) | 7 | 7 | 7 | 0 |
| Interfacial tension (mNm) | 1 | 1 | 1 | 27 |
| $D_{def}$ min/average/max (μm) | 0.04/0.3/1.1 | 0.04/0.3/1.1 | 0.04/0.3/1.1 | 1/8/30 |
| Diameter of the pores of the filters (μm) | 5 | 1.2 | 0.2 | 1.2 |
| Oil content of the filtrate (ppm) | 196 | 33 | 4 | 0.5 |

Third Example

As the third example, water containing 200 ppm of droplets of crude (of oil) with a diameter of 8 μm with 0.5 g/L of a sodium alkyl ether sulfate surfactant and 7 g/L of Na$_2$CO$_3$ (base) was filtered. The results are presented in Table 4 and show that the presence of the surfactant and of the base lowers the crude/water interfacial tension. Filtration becomes inefficient if the pore size is not reduced in view of the deformability conferred on the droplets D$_{def}$ calculated by the method according to the invention on the basis of the threshold capillary number for the case of water with neither alkali nor surfactant (column on the right of Table 4). For this example, a filter with pores with a diameter less than 0.06 μm gives efficient filtration. This table shows the minimum, average and maximum values of the diameter of deformability of the droplets, so as to take into account a droplet size distribution representative of the oil droplets present in the aqueous liquid.

TABLE 4

| | Third example | | | |
|---|---|---|---|---|
| Concentration of surfactant (ppm) | 500 | 500 | 500 | 0 |
| Na$_2$CO$_3$ concentration (g/L) | 7 | 7 | 7 | 0 |
| Interfacial tension (mNm) | 0.2 | 0.2 | 0.2 | 27 |
| D$_{def}$ min/average/max (μm) | 0.007/0.06/0.22 | 0.007/0.06/0.22 | 0.007/0.06/0.22 | 8 |
| Diameter of the pores of the filters (μm) | 5 | 1.2 | 0.2 | 1.2 |
| Oil content of the filtrate (ppm) | 200 | 143 | 103 | 0.5 |

Thus, the method according to the invention gives efficient treatment of the water, owing to the choice of a suitable filter that allows considerable removal of the oil droplets contained in the water, regardless of what other compounds are present in the water.

The invention claimed is:

1. A method for treating an aqueous liquid to be filtered, the aqueous liquid to be filtered comprising oil droplets and at least one surfactant and/or at least one base, wherein the following steps are carried out:
   a) determining the interfacial tension between the oil droplets and the water in the aqueous liquid to be filtered, the interfacial tension being dependent upon the surfactant and/or the base;
   b) determining a pore size threshold radius R$_{def}$ of a filter for retaining the oil droplets from the aqueous liquid to be filtered, the pore size threshold being a function of interfacial tension by:
      b1) determining the viscosity η, droplet radius R and interfacial tension Γ of a test aqueous liquid having a given concentration of the at least one surfactant and/or at least one base, the test aqueous liquid being an aqueous liquid having a concentration of the at least one surfactant and/or at least one base such that the droplets are efficiently filtered by a filter whose pores are of a specified size;
      b2) calculating a threshold capillary number Ca* using a formula of the type:

$$Ca^* = \frac{\eta \dot{\gamma} R}{\Gamma},$$

wherein γ' is the shear rate applied to the oil droplet
      b3) calculating R$_{def}$ from a formula:

$$R_{def} = Ca^* \frac{\Gamma}{\eta \dot{\gamma}},$$

where η is the viscosity of the aqueous liquid to be filtered, γ' is the shear rate applied to the oil droplet and Γ is the interfacial tension of the aqueous liquid to be filtered;
   c) treating the aqueous liquid to be filtered by filtration using a filter for which the size of the pores is less than or equal to the pore size threshold.

2. The method as claimed in claim 1, wherein the viscosity of the aqueous liquid is determined by measurement using a rheometer.

3. The method as claimed in claim 1, wherein the interfacial tension is determined by measurement, or as a function of the concentration and of the type of the surfactant and/or of the base.

4. The method as claimed in claim 1, wherein the shear rate is determined as a function of the flow rate of the aqueous liquid in the filter.

5. The method as claimed in claim 1, wherein said filtration is a dead-end or tangential membrane filtration with flow of said aqueous liquid.

6. The method as claimed in claim 5, wherein the filter is a polymeric, or metallic or ceramic membrane.

7. A method for treating a petroleum effluent, wherein the following steps are carried out:
   d) separating the phases of the petroleum effluent, to separate at least an aqueous liquid phase, a liquid oil phase and a gas phase; and
   e) treating the aqueous liquid phase by the method for treating an aqueous liquid according to claim 1, the aqueous liquid comprising oil droplets and at least a surfactant and/or base of the injected fluid.

8. A method for assisted recovery of hydrocarbons from an underground formation, wherein the following steps are carried out:
   f) injecting a fluid into the underground formation, the injected fluid comprising at least one surfactant and/or base;
   g) recovering a petroleum effluent from the underground formation, the petroleum effluent comprising at least one part of the injected fluid;
   h) separating the phases of the petroleum effluent, to separate at least an aqueous liquid phase, a liquid oil phase and a gas phase; and
   i) treating the aqueous phase by the method for treating an aqueous liquid as claimed in claim 1, the aqueous liquid comprising oil droplets and at least one surfactant and/or base of the injected fluid.

9. The method as claimed in claim 1, wherein step c) treating the aqueous liquid to be filtered by filtration is carried out using a filter for which the size of the pores is less than 0.9 times the pore size threshold.

* * * * *